(12) United States Patent  
Garimella et al.

(10) Patent No.: US 9,063,086 B1  
(45) Date of Patent: Jun. 23, 2015

(54) METHOD AND APPARATUS FOR COMPRESSING IONS

(71) Applicants: Sandilya V. B. Garimella, Richland, WA (US); Yehia M. Ibrahim, Richland, WA (US); Gordon A. Anderson, Benton City, WA (US); Richard D. Smith, Richland, WA (US)

(72) Inventors: Sandilya V. B. Garimella, Richland, WA (US); Yehia M. Ibrahim, Richland, WA (US); Gordon A. Anderson, Benton City, WA (US); Richard D. Smith, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 26 days.

(21) Appl. No.: 14/179,329

(22) Filed: Feb. 12, 2014

(51) Int. Cl.
```
G01N 27/62      (2006.01)
H01J 49/00      (2006.01)
H01J 49/10      (2006.01)
```

(52) U.S. Cl.
CPC .......... *G01N 27/622* (2013.01); *H01J 49/0027* (2013.01); *H01J 49/10* (2013.01)

(58) Field of Classification Search
USPC ................................................. 250/286, 287
See application file for complete search history.

(56) References Cited

U.S. PATENT DOCUMENTS

| | | | |
|---|---|---|---|
| 5,457,316 A * | 10/1995 | Cohen et al. | 250/286 |
| 5,572,035 A | 11/1996 | Franzen | |
| 6,107,328 A | 8/2000 | Parsons | |
| 6,960,760 B2 | 11/2005 | Bateman et al. | |
| 7,365,317 B2 | 4/2008 | Whitehouse et al. | |
| 7,391,021 B2 | 6/2008 | Stoermer et al. | |
| 7,786,435 B2 | 8/2010 | Whitehouse et al. | |
| 7,838,826 B1 | 11/2010 | Park | |
| 7,888,635 B2 | 2/2011 | Belov et al. | |
| 8,049,169 B2 | 11/2011 | Satake et al. | |
| 8,222,597 B2 | 7/2012 | Kim et al. | |
| 8,296,078 B1 * | 10/2012 | Pfeifer et al. | 702/24 |
| 2004/0026611 A1 | 2/2004 | Bateman et al. | |
| 2007/0138384 A1 | 6/2007 | Keiser | |
| 2010/0127164 A1 * | 5/2010 | Atkinson et al. | 250/282 |
| 2011/0049357 A1 | 3/2011 | Giles | |
| 2011/0192969 A1 | 8/2011 | Verentchikov | |

FOREIGN PATENT DOCUMENTS

EP        1825495 B1      11/2011

OTHER PUBLICATIONS

Nieminen, A., et al., Beam cooler for low-energy radioactive ions, Nuclear Instruments and Methods in Physics Research A, 469, 2001, 244-253.

Pervukhin, V. V., et al., Ion Peak Narrowing by Applying Additional AC Voltage (Ripple Voltage) to FAIMS Extractor Electrode, J Am Soc Mass Spectrom, 21, 2010, 47-52.

* cited by examiner

*Primary Examiner* — Kiet T Nguyen
(74) *Attorney, Agent, or Firm* — A.J. Gokcek

(57) ABSTRACT

A method and apparatus for compressing ions inside an ion mobility device is disclosed. Ions are introduced into the mobility device. The ions are subjected to a non-constant electric field to form a potential gradient along a portion of the device so that ions with similar mobilities bunch together into sharper peaks while maintaining separation between other ions. The potential gradient progressively increases or decreases along the length of the device.

18 Claims, 10 Drawing Sheets

| m/z | Reduced ion mobility [m2/Vs] | Mobility at 4torr [m2/Vs] | Diffusion coeff | Tof before ions enter compressor [s] | [V/m] | velocity [m/s] | dx = sqrt(9Dt) [mm] | Distance ions move in tof [mm] | Separation [mm] |
|---|---|---|---|---|---|---|---|---|---|
| 622 | 1.17E-04 | 2.22E-02 | 0.00052278 | 0.005 | 1800 | 4.00E+01 | 4.85026647 | 2.00E+02 | 75.24 |
| 922 | 0.000097 | 1.84E-02 | 0.000476281 | 0.005 | 1800 | 3.32E+01 | 4.629539982 | 1.66E+02 | 41.04 |
| 1222 | 0.000085 | 1.62E-02 | 0.00041736 | 0.005 | 1800 | 2.91E+01 | 4.333725854 | 1.45E+02 | 20.52 |
| 1522 | 0.000073 | 1.39E-02 | 0.000358438 | 0.005 | 1800 | 2.50E+01 | 4.016182155 | 1.25E+02 | 0.00 |

Figure 5

METHOD AND APPARATUS FOR COMPRESSING IONS

STATEMENT REGARDING FEDERALLY SPONSORED RESEARCH OR DEVELOPMENT

This invention was made with Government support under Contract DE-AC05-76RLO1830 awarded by the U.S. Department of Energy and Grant Nos. U24 CA1690019 and P41 GM103493 awarded by the National Institutes of Health. The Government has certain rights in the invention.

TECHNICAL FIELD

This invention relates to ion mobility spectrometry. More specifically, this invention relates to methods of compressing diffuse ion peaks with similar mobilities into sharper peaks while maintaining separation between other separated ion peaks.

BACKGROUND OF THE INVENTION

One of the significant requirements in a complex biological sample/mixture analysis, proteomics and other omics applications is the need to pre-process highly complex mixtures of molecules prior to mass spectrometry (MS) analysis. By coupling ion mobility spectrometry (IMS) to MS, gas phase separation of the mixture is achieved using ionic mobility differences and also an orthogonal dimension of analysis can be obtained.

However, the peak separation or resolving power of a given IMS device to separate two components of the mixture is limited by the fact that the ionic species diffuse with time. While ions drift over a long drift section of a mobility device, they separate out based on their mobilities. However individual peaks also broaden due to diffusion.

The increasing plume thickness with increasing time, if curtailed, would increase the separation characteristics significantly. The problem being addressed is to periodically bunch individual ion mobilities into tighter ion packets, while maintaining the time separation (resolution) between other ion packets (mobilities).

SUMMARY OF THE INVENTION

In accordance with one embodiment of the present invention, a method of compressing ions inside an ion mobility device is disclosed. The method includes introducing ions into the ion mobility device. The method also includes subjecting the ions to a non-constant electric field to form a potential gradient along a portion of the device so that ions with similar mobilities bunch together into sharper peaks while maintaining separation between other ions.

In one embodiment, the potential gradient is a DC gradient. In another embodiment, the potential gradient progressively increases or decreases along the length of the device. The potential gradient along the length of the device is between 0 to about 5,000 volts/mm.

In one embodiment, the ions have a mass to charge ratio in the range of 1 to about 100,000 and a drift time through the device in the range of about 0 to about 60 seconds.

At least a portion of the device is maintained at a pressure in the range of about $10^{-3}$ torr to atmospheric pressure.

The device may be coupled to at least one of the following: a charge detector, an optical detector, and a mass spectrometer.

The ions inside the device may be formed using at least one of the following: photoionization, Corona discharge, laser ionization, electron impact, field ionization, chemical ionization, and electrospray.

In one embodiment, the ions are introduced from outside the device.

In another embodiment of the present invention, an apparatus is disclosed. The apparatus includes an ion mobility device wherein ions are provided to the device. The apparatus also includes a non-constant electric field applied to the device to form a potential gradient along a portion of the device so that ions with similar mobilities bunch together into sharper peaks while maintaining separation between other ions.

BRIEF DESCRIPTION OF THE DRAWINGS

FIG. 5 is a table of calculations for the relative position of each ion packet—m/z 622, 922, 1222, and 1522—in FIG. 1A.

DETAILED DESCRIPTION OF THE PREFERRED EMBODIMENTS

The present invention relates to methods and apparatuses for compressing an ion packet inside or within an ion mobility spectrometry (IMS) device, achieving high IMS resolving power while maintaining the peak resolution.

In one embodiment, a relatively broad ion packet in gas phase is subjected to a non-linear potential profile with a decreasing electric drift field. The ions in the high field region move faster than ions in the low field region, resulting in peak bunching. By using non-constant electric fields (e.g., DC) peak broadening or diffusion can be overcome. Due to non-linear potential profile, ions in different regions move with different velocities. Therefore, when applied suitably these fields can be used to bunch together ions in a broad peak to a narrow packet.

When the different mobilities for different ion packets are sufficiently separated, the bunching is applied locally.

Figure 1A:
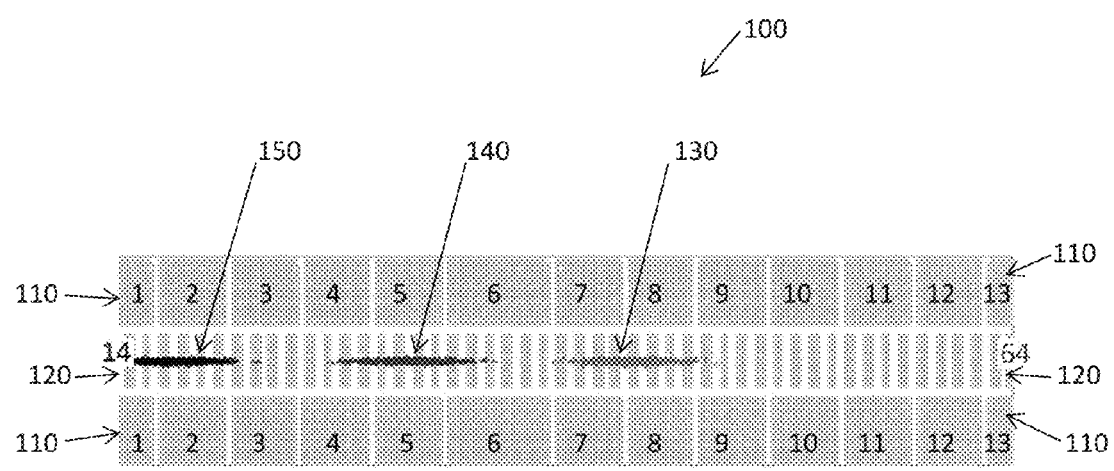
FIG. 1A is a schematic showing the initial conditions and relative positions of ion packets drifting through an ion mobility device, in accordance with one embodiment of the present invention.

FIG. 1A is a schematic showing the initial conditions and relative positions of ion packets drifting through an ion mobility device 100, in accordance with one embodiment of the present invention. The device 100 includes an outer array of electrodes 110 and an inner array of electrodes 120. Alternatively, the device 100 may be any ion mobility or manipulation device as described in U.S. patent application Ser. No. 14/146,922, filed on, Jan. 3, 2014, the contents of which are incorporated by reference. The device 100 also shows the relative positions of the three peaks 130, 140, 150 in a drift section of the device 100. In this example, the peak 130 has an m/z of 922. The peak 140 has an m/z of 1222, and the peak 150 has an m/z of 1522. The relative positions of each peak 130, 140, and 150 also include the peak widths after about 5 ms of drift through a constant field of about 18 V/cm. The calculations for the relative positions of the mobility packets and plume spread are given in FIG. 5. The RF frequency applied to the device 100 was about 0.8 MHz to fully confine the m/z 1522 ion peaks.

Figure 1B:
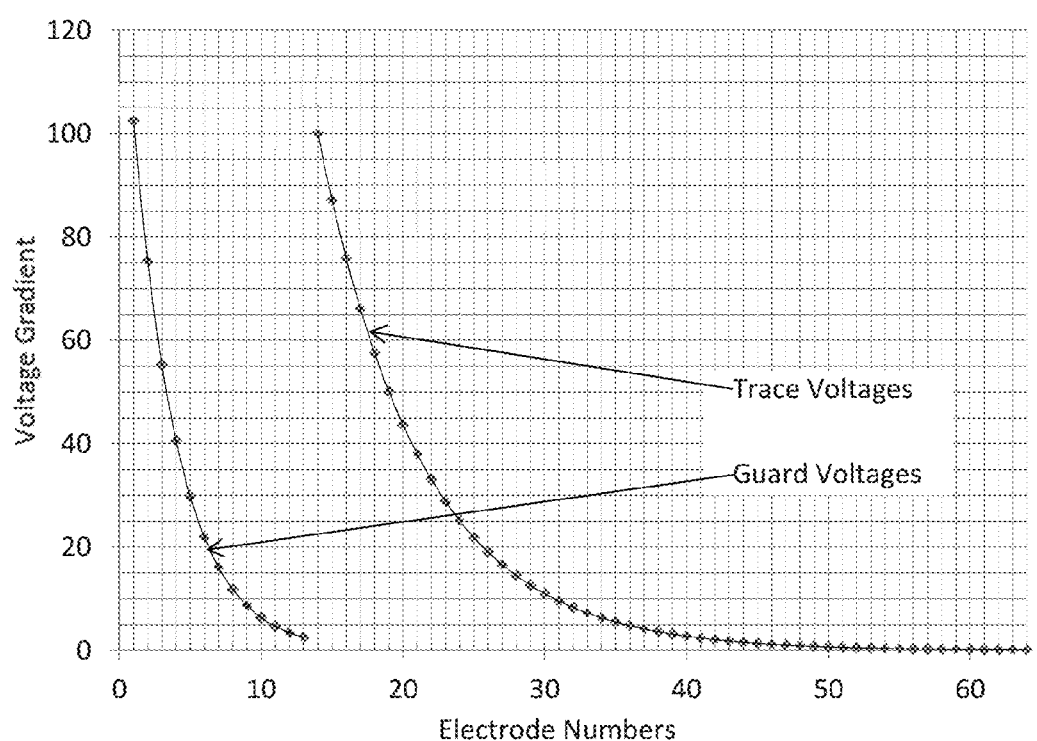
FIG. 1B is a graph showing the applied potentials on the Y axis and the electrode numbers (1-13 and 14-64 from FIG. 1A) on the X axis.

FIG. 1B is a graph showing the applied potentials (on the drift section of the device 100 in FIG. 1A) on the Y axis and the electrode numbers on the X axis. The guard voltages refer to the outer array of electrodes 110 labeled 1 through 13 in FIG. 1A. The trace voltages refer to the inner array of electrodes labeled 14 through 64 in FIG. 1A. The voltage profile along the electrodes is exponential.

Figure 2A:
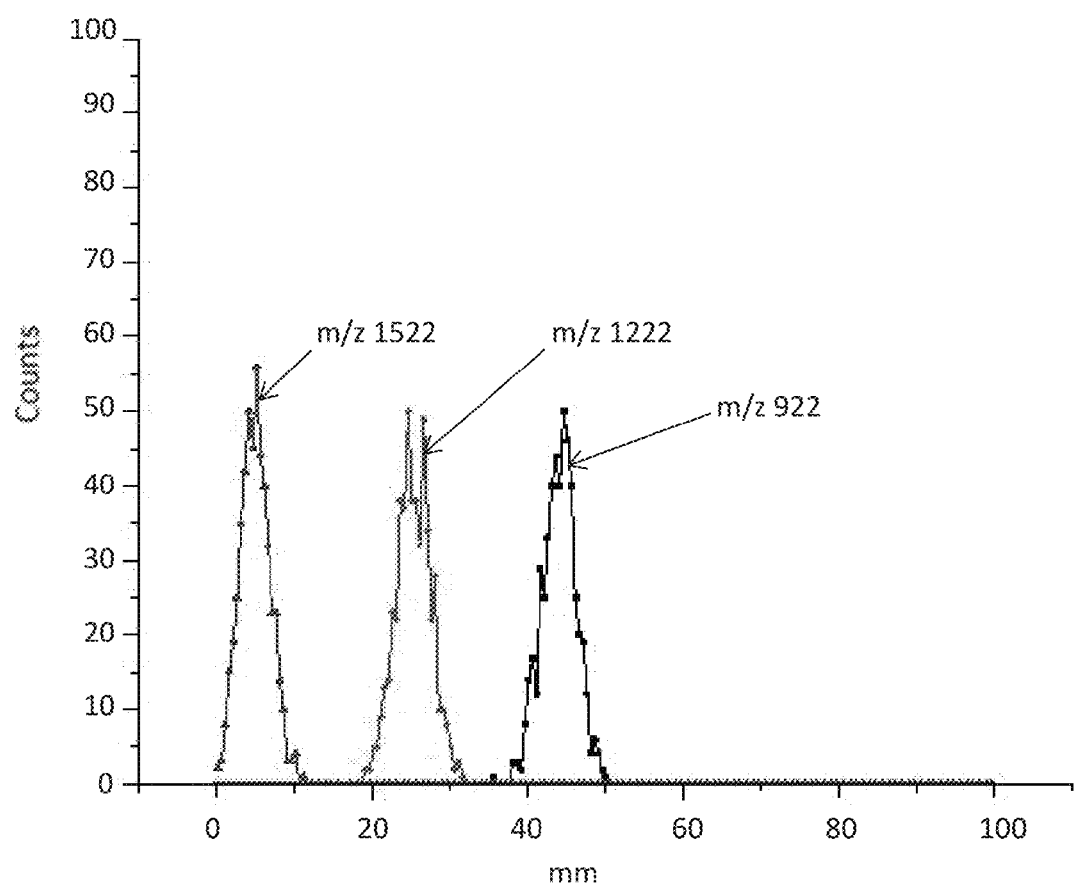
FIG. 2A is a graph showing the initial spatial spreads of the ion peaks.

FIG. 2A is a graph showing the initial spatial spreads of the ion peaks—m/z of 922, m/z of 1222, and m/z of 1522—subjected to a constant electric field.

Figure 2B:
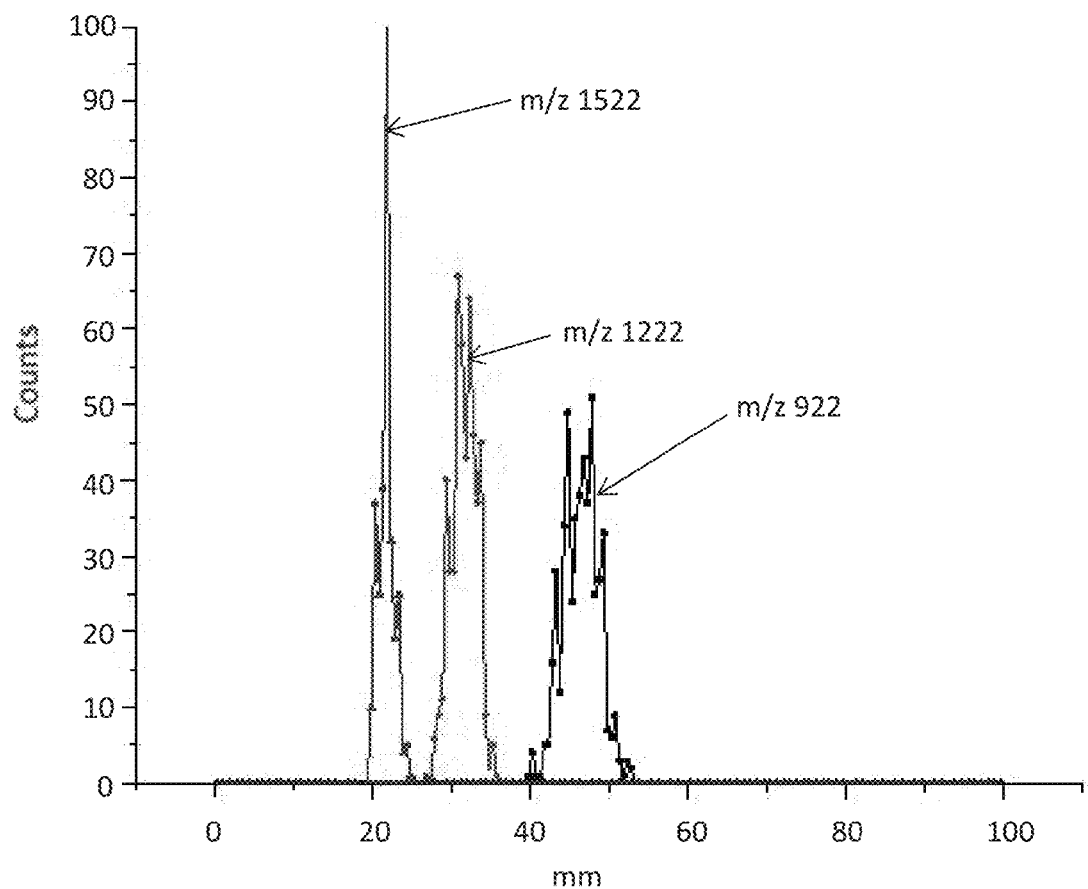
FIG. 2B is a graph showing the spatial spreads of the ion peaks after about 500 μs of motion through a non-constant electric field.

FIG. 2B is a graph showing the spatial spreads of the ion peaks after about 500 µs of motion through a non-constant electric field applied over the length of the device 100 of FIG. 1A. As shown in FIG. 2B, the ions travel through different gradients. The peak 1522 m/z bunches the maximum because it falls through a higher potential difference in the same time. The peak 1222 m/z exhibits some drift and compresses marginally. The peak 922 m/z—the lowest m/z peak—is in a region with practically zero potential drop or field gradient and does not undergo much drift. Thus, peak compression is negligible for the 922 m/z ion packet.

Figure 3A:
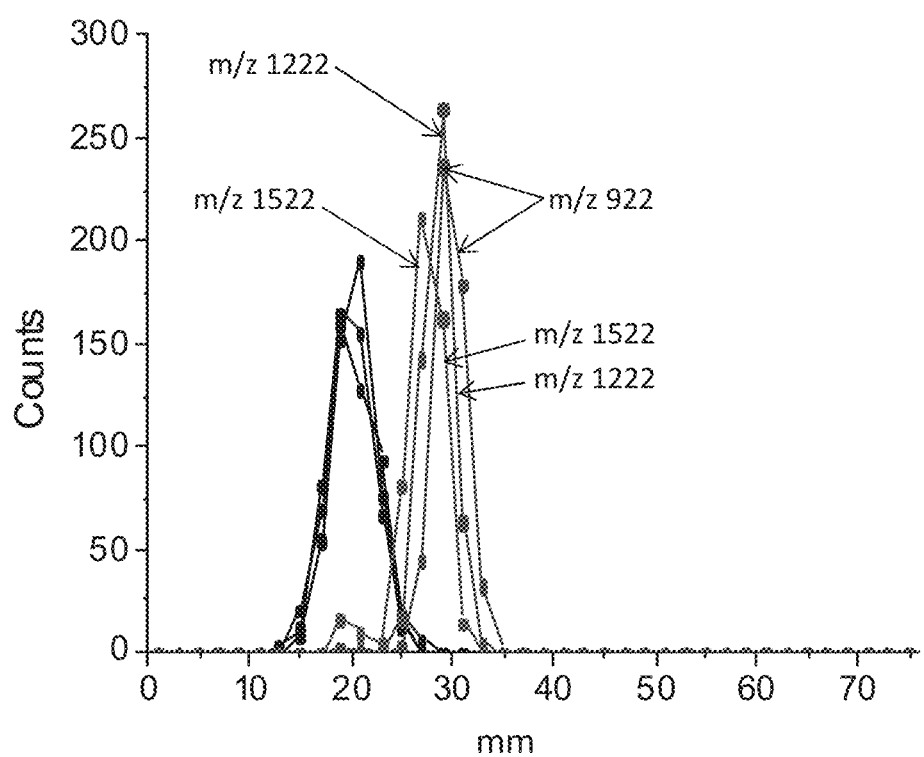
FIG. 3A shows the peak behavior when all the peaks fall through the same potential drop applied for approximately 500 μs.

FIG. 3A shows the peak behavior when all the peaks fall through the same potential drop. The compression is applied for about 500 µs—i.e., the ions take approximately 500 µs to move through an approximately 10 mm distance. There is an approximately 30 volts drop over the approximately 10 mm fly distance of the ions.

In FIG. 3A, the ion packets seem to be in the same space location initially. The ion packets are actually separated in time domain. At different times, all ion packets traverse through the same potential gradient imposed on the device 100 (FIG. 1A).

Figure 3B:
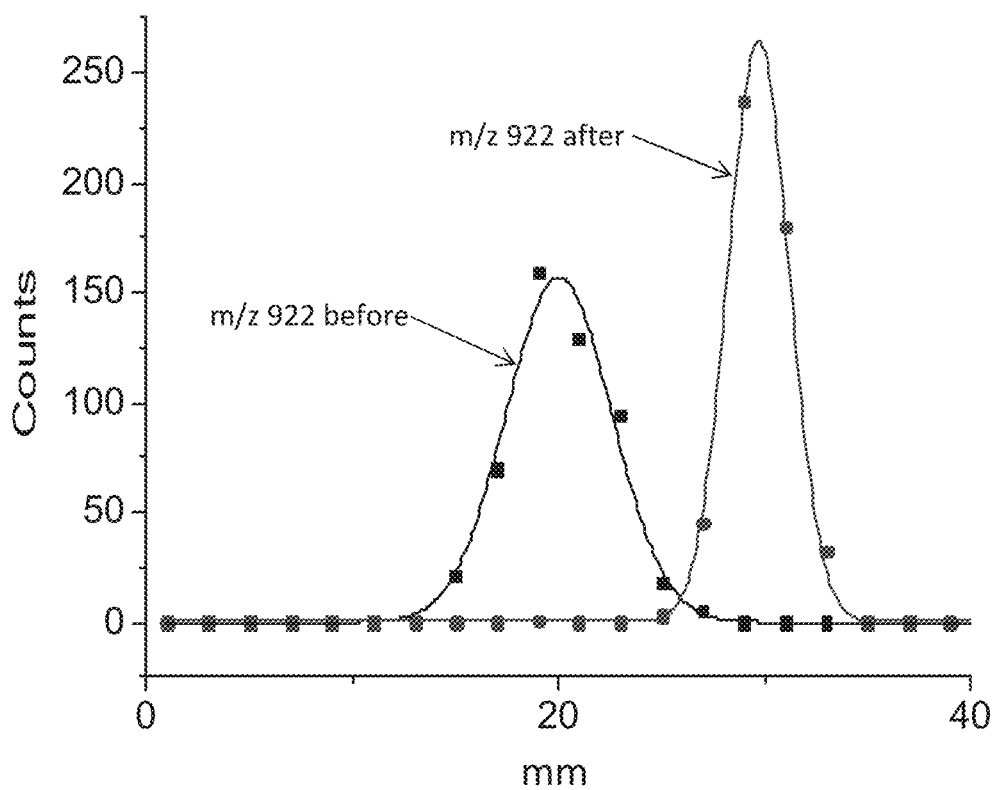
FIG. 3B shows significant improvement in the peak resolving power for ions having m/z 922 before and after the compression.

FIG. 3B shows significant improvement in the peak resolving power for ions having m/z 922 before and after the compression. Before compression, the full-width half-maximum or FWHM of the spatial distribution of the 992 m/z ions was 6.0 mm. After compression, the FWHM was 3.5 mm.

Figure 3C:
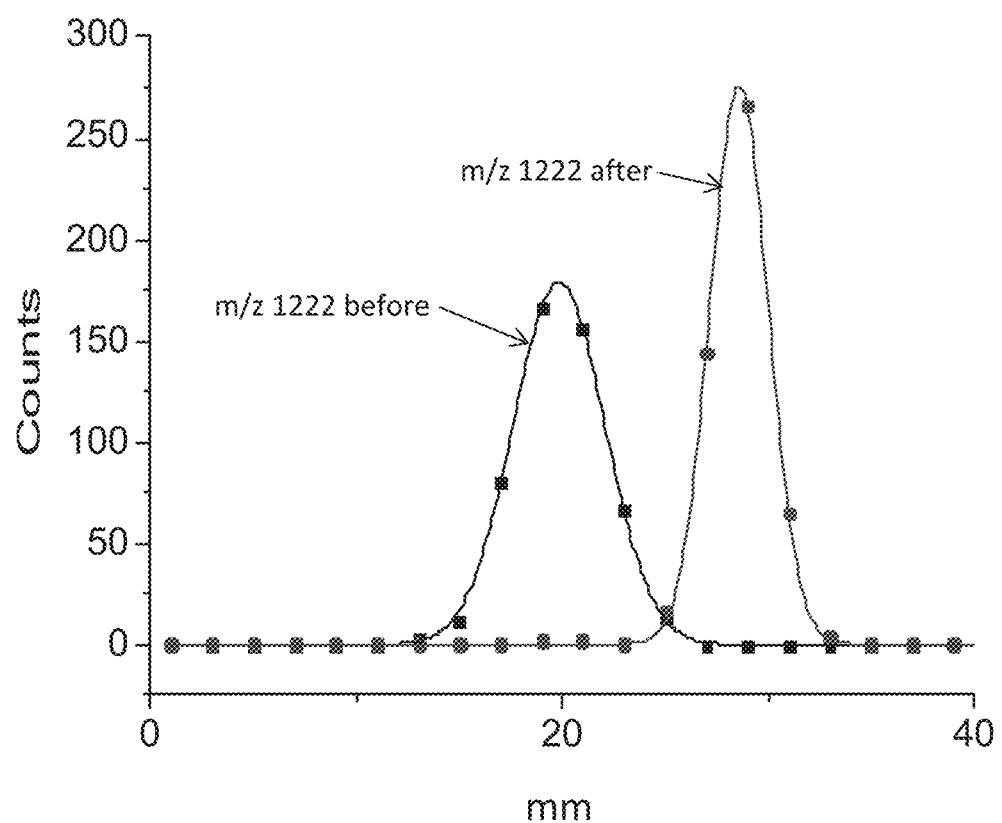
FIG. 3C shows significant improvement in the peak resolving power for ions having m/z 1222 before and after the compression.

FIG. 3C shows significant improvement in the peak resolving power for ions having m/z 1222 before and after the compression. Before compression, the FWHM of the spatial distribution of the 1222 m/z ions was 5.3 mm. After compression, the FWHM was 3.3 mm.

Figure 3D:
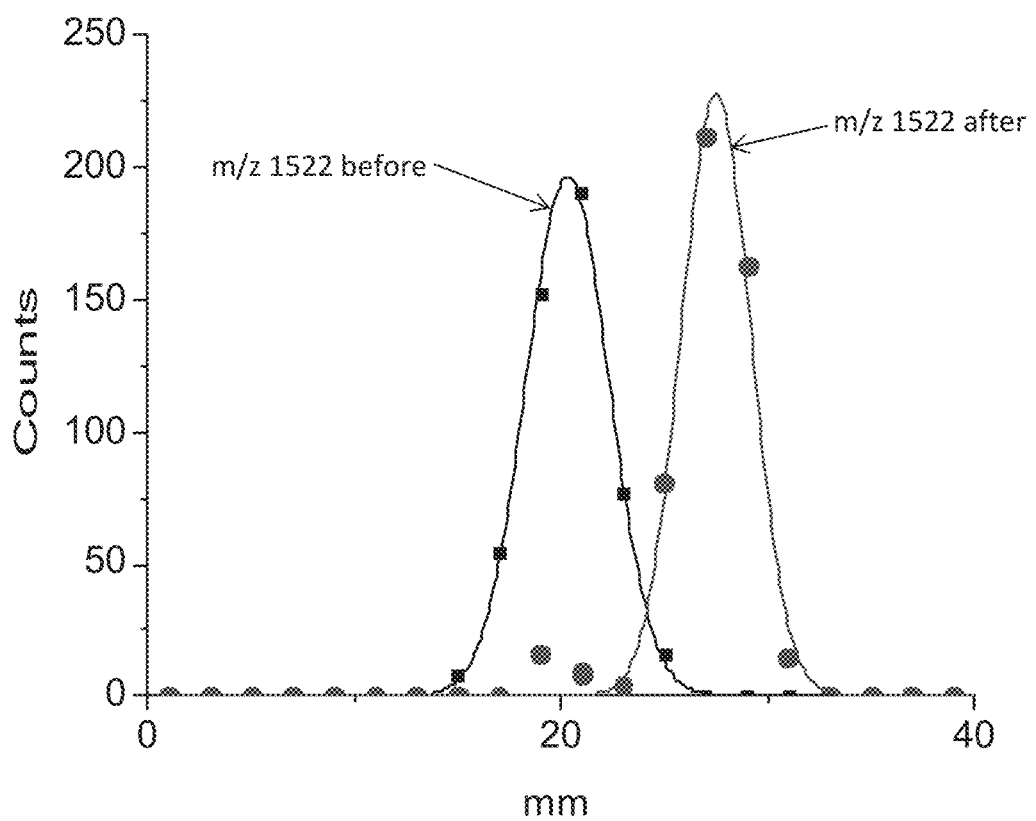
FIG. 3D shows significant improvement in the peak resolving power for ions having m/z 1522 before and after the compression.

FIG. 3D shows significant improvement in the peak resolving power for ions having m/z 1522 before and after the compression. Before compression, the FWHM of the spatial distribution of the 1522 m/z ions was 4.7 mm. After compression, the FWHM was 4.0 mm.

Figure 4:
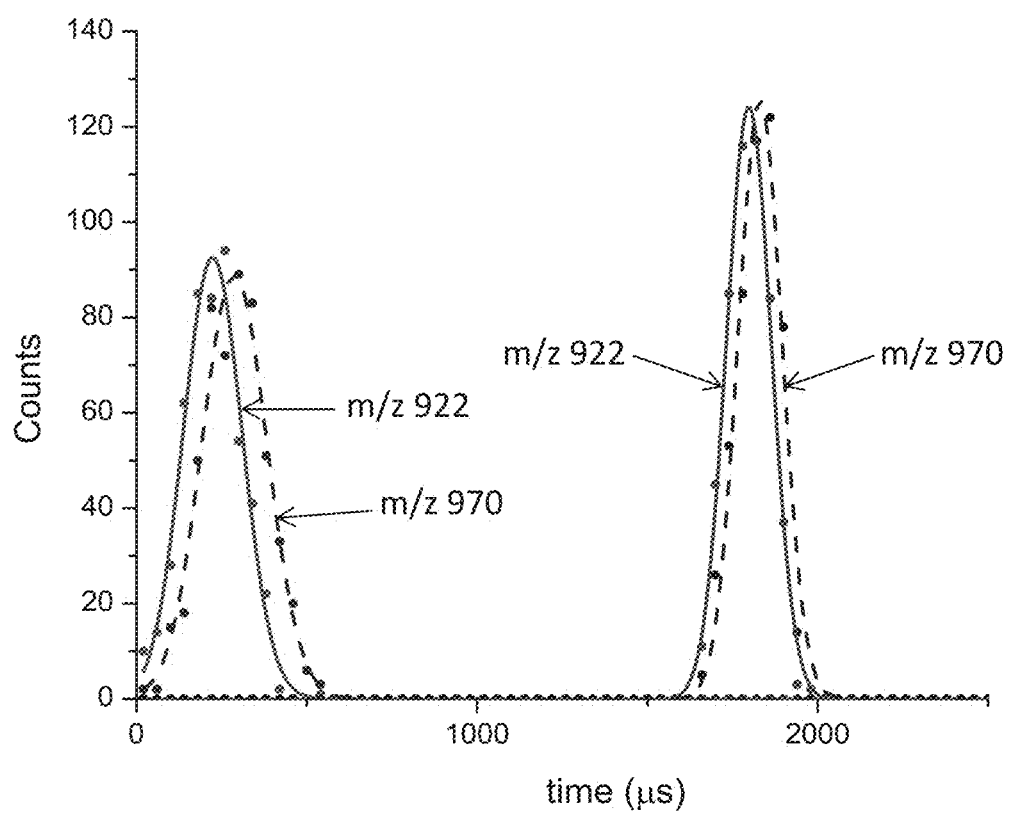
FIG. 4 shows significant improvement in the peak resolving power for two packets of ions before and after the compression is applied for about 1 ms.

FIG. 4 shows significant improvement in the peak resolving power for two packets of ions—m/z 922 and m/z 970—before and after the compression is applied for about 1 ms. The two close peaks have about 1% difference in mobilities. At time zero, the ions are assumed to travel approximately 500 µs before simulation. From time zero to about 500 µs, a linear gradient of about 13 V/cm is applied during the simulation. Before the non-constant electric field is applied, the two ion peaks have a FWHM of 203.3 µs, a time resolving power (R) of 26, and a separation between peaks or an initial resolution ($\Delta R_{initial}$) of 0.3. From time 500 µs to about time 1500 µs, the non-constant electric field is applied. From time 1500 µs to about 2000 µs, the linear field of 13 V/cm is applied till splatting at a plane to collect ion statistics. After the non-constant field is applied, the two ion peaks have an FWHM of 154.6 µs, an R of 44, and a final resolution ($\Delta R_{final}$) of 0.2.

As shown in FIG. 4, there is significant improvement in resolving power of the two peaks during simulation when the non-linear electric field is applied. Some decrease in peak resolution is seen. However, when applied to well-separated peaks, the time separation is not lost and resolving power increases significantly.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. A method of compressing ions inside an ion mobility device, comprising:
   a. introducing ions into the ion mobility device;
   b. applying a non-constant electric field to the ion mobility device to form a potential gradient along a portion of the device so that ions with similar mobilities bunch together into sharper peaks while maintaining separation between other ions with different mobilities.

2. The method of claim 1 wherein the potential gradient is a DC gradient.

3. The method of claim 1 wherein the potential gradient progressively increases or decreases along the length of the device.

4. The method of claim 1 wherein the potential gradient along a length of the device is between 0 to about 5,000 volts/mm.

5. The method of claim 1 wherein the ions have a mass to charge ratio in the range of 1 to about 100,000.

6. The method of claim 1 wherein the ions have a drift time through the device in the range of about 0 to about 60 seconds.

7. The method of claim 1 wherein at least a portion of the device is maintained at a pressure in the range of about $10^{-3}$ torr to atmospheric pressure.

8. The method of claim 1 wherein the device is coupled to at least one of the following: a charge detector, an optical detector, and a mass spectrometer.

9. The method of claim 1 wherein the ions inside the device are formed using at least one of the following: photoionization, Corona discharge, laser ionization, electron impact, field ionization, chemical ionization, and electrospray.

10. An apparatus comprising:
    a. an ion mobility device wherein ions are provided to the device; and b. a non-constant electric field applied to the device to form a potential gradient along a portion of the device so that ions with similar mobilities bunch together into sharper peaks while maintaining separation between other ions with different mobilities.

11. The apparatus of claim 10 wherein the potential gradient is a DC gradient.

12. The apparatus of claim 10 wherein the potential gradient progressively increases or decreases along the length of the device.

13. The apparatus of claim 10 wherein the potential gradient along a length of the device is between 0 to about 5,000 volts/mm.

14. The apparatus of claim 10 wherein the ions have a mass to charge ratio in the range of 1 to about 100,000.

15. The apparatus of claim 10 wherein the ions have a drift time through the device in the range of about 0 to about 60 seconds.

16. The apparatus of claim 10 wherein at least a portion of the device is maintained at a pressure in the range of about $10^{-3}$ torr to atmospheric pressure.

17. The apparatus of claim 10 wherein the device is coupled to at least one of the following: a charge detector, an optical detector, and a mass spectrometer.

18. The apparatus of claim 10 wherein the ions inside the device are formed using at least one of the following: photo-ionization, Corona discharge, laser ionization, electron impact, field ionization, chemical ionization, and electrospray.

* * * * *